United States Patent [19]

Fraleigh

[11] 4,281,546

[45] Aug. 4, 1981

[54] VARIABLE VOLUME SAMPLE CUTTER AND METHOD OF USE

[76] Inventor: M. Foster Fraleigh, 112 Lakeshore Dr., North Palm Beach, Fla. 33408

[21] Appl. No.: 57,392

[22] Filed: Jul. 13, 1979

[51] Int. Cl.³ ............................................ G01N 1/04
[52] U.S. Cl. .................................... 73/864.44; 83/17; 83/19; 83/21; 83/143; 83/176; 83/623; 83/919; 264/153; 425/292; 425/298
[58] Field of Search ...................... 264/153; 83/17, 19, 83/20, 21, 143, 176, 588, 623, 919; 73/423 R, 425, 425.2; 425/292, 298

[56] References Cited

U.S. PATENT DOCUMENTS

| 2,255,116 | 9/1941 | Helmstoedter | 264/153 |
| 2,375,518 | 5/1945 | Bolle | 264/153 |
| 3,418,690 | 12/1968 | Edwards | 264/153 |

*Primary Examiner*—James B. Lowe
*Attorney, Agent, or Firm*—Oldham, Oldham, Hudak & Weber

[57] ABSTRACT

An apparatus and method for cutting elastomeric material into volumetric elastomer samples is disclosed. These volumetric samples may be reproduced at identical mass for precision testing purposes. The volumetric samples are reproducible for such precision purposes by the use of a volumetric adjustment mechanism which determines the volume of the cavity into which elastomeric material is compressed before cutting. The apparatus also has a moving cutting mechanism with a contoured cutting area, which in combination with the volumetric adjustment apparatus, removes deleterious air bubbles and other deformities prior to cutting the elastomeric material. The volumetric adjustment apparatus is housed within a die apparatus, which has a damping mechanism to permit complete manipulation of the elastomer prior to cutting the elastomer into the volumetric plug. After the cutting of the plug has occurred, the ejection apparatus pushes the volumetric plug from the cavity whereupon another cycle is begun. The apparatus may also treat and cure uncured elastomeric material within the volumetric cavity by the application of heat sources to the apparatus surrounding the cavity.

13 Claims, 2 Drawing Figures

VARIABLE VOLUME SAMPLE CUTTER AND METHOD OF USE

BACKGROUND OF THE INVENTION

This invention relates to the apparatus and method for cutting elastomeric material into volumetric samples in such a manner that the elastomeric material has a homogeneous composition without air bubbles and may be reproduced at accurate masses by variable volumetric adjustment.

Heretofore, many attempts have been made to produce apparatus to effectively separate a portion of material from stock with a die cutting or punching mechanism. For example, U.S. Pat. Nos. 120,162; 1,506,480; 1,166,613; 1,755,191; 2,049,624; and 2,369,896 disclose a variety of cutting mechanisms for materials. Should the cutting apparatus employ a punching mechanism, U.S. Pat. Nos. 295,227; 904,714; and 3,465,634 disclose a pointed punch configuration which forms a conical contact with the material being cut prior to the actual cutting edge making contact with a stationary surface. In a different direction, punching mechanisms have taught a curved surface to engage the stationary cutting edge. U.S. Pat. Nos. 3,288,665 and 4,123,956 have disclosed such a feature.

The punching and die cutting mechanisms so disclosed in the art have relied upon the swiftness of mechanism and the sharpness of cutting surface to achieve the desired product. Such reliance has been proved to be misplaced, wherein the control over quality of the cut product with certain materials has proved to be volumetrically inaccurate.

Once the material has been cut or punched, improvements to the basic punch design have been utilized to remove the cut material or slug from the cutting or punching area. U.S. Pat. Nos. 3,296,905 and 3,823,630 have provided means for removing the punched slug from the cutting area. However, these mechanisms do not serve any purpose during the cutting or punching operation.

When elastomeric material, particularly uncured or green rubber or elastomeric materials of a similar resiliency, are placed in a punching mechanism according to the designs described in the art, the material does not achieve a quality cut or punch because of the nature of its inherent resiliency. Particularly, the elastomeric material is unevenly spread under the pressure of the machine prior to the cut. Therefore, the need exists for additional designs and mechanisms for the apparatus to cut or punch elastomeric material to overcome the defects in cutting operations when a resilient material is being manipulated.

Whenever elastomer plugs or samples must be reproducible for precision purposes, the cavity into which the elastomeric material entered prior to cutting must be of a specific and accurate volume. This volumetric requirement is not found in the art, and the reproducibility of volumetric samples for precision purposes is greatly desired.

OBJECTS OF THE INVENTION

Therefore, it is an object of this invention to provide a method for cutting elastomeric material such that the elastomeric plug or sample is volumetrically accurate for precision purposes.

It is another object of the invention to provide an apparatus for the cutting of elastomeric material into volumetric samples or plugs, such that the volumetric accuracy of the plug or sample is reproducible.

It is yet another object of the invention to provide an apparatus for the cutting of elastomeric plugs or samples for precision testing purposes, such that the cavity into which the elastomeric material is compressed has a volumetric capacity which is variably determined by the apparatus.

Still another object of this invention is to provide a method for the cutting of elastomeric material, such that the volumetric elastomeric plug or sample so cut is homogeneous in structure and lacking defective structural inadequacies.

Yet another object of the invention is to provide an apparatus for cutting elastomeric material into volumetric samples, wherein the surface of the cutting tool is formed to effectuate removal of air bubbles from the material within the cutting area, to maintain the volumetric accuracy of the cavity as adjusted by the variable sample adjustment apparatus.

Moreover, it is another object of the invention to provide a method for the cutting of elastomeric material utilizing the apparatus designed specifically therefor, wherein the combination of the cutting surface of the cutting tool with the volumetrically variable adjustment apparatus effectuates a homogeneous compression of the elastomeric material prior to a concentric cutting operation to produce a volumetric sample for precision testing purposes.

These and other objects, which will become apparent as the detailed description of the preferred embodiments proceeds, are achieved by: an apparatus for the variable cutting of volumetric samples from elastomeric material, comprising: (a) a fixed frame having a forming post housing; (b) a die cutting apparatus having an elastomer-manipulative cutting surface; (c) a die receiving apparatus tensionally mounted on said frame and having a die with an internal hollow having a dimension; and (d) a volumetric sample adjustment apparatus having a movable forming post and adjustment means for moving said forming post, said forming post having a contact surface which resides in said internal hollow of said die, so that said movable forming post and said die dimension determine a volumetric cavity into which the elastomeric material may be manipulated prior to cutting the material into the volumetric sample.

DESCRIPTION OF THE DRAWINGS

For a greater understanding of the scope of the invention, attention is directed to the Figures, wherein.

DETAILED DESCRIPTION OF THE PREFERRED EMBODIMENTS

Figure 1:
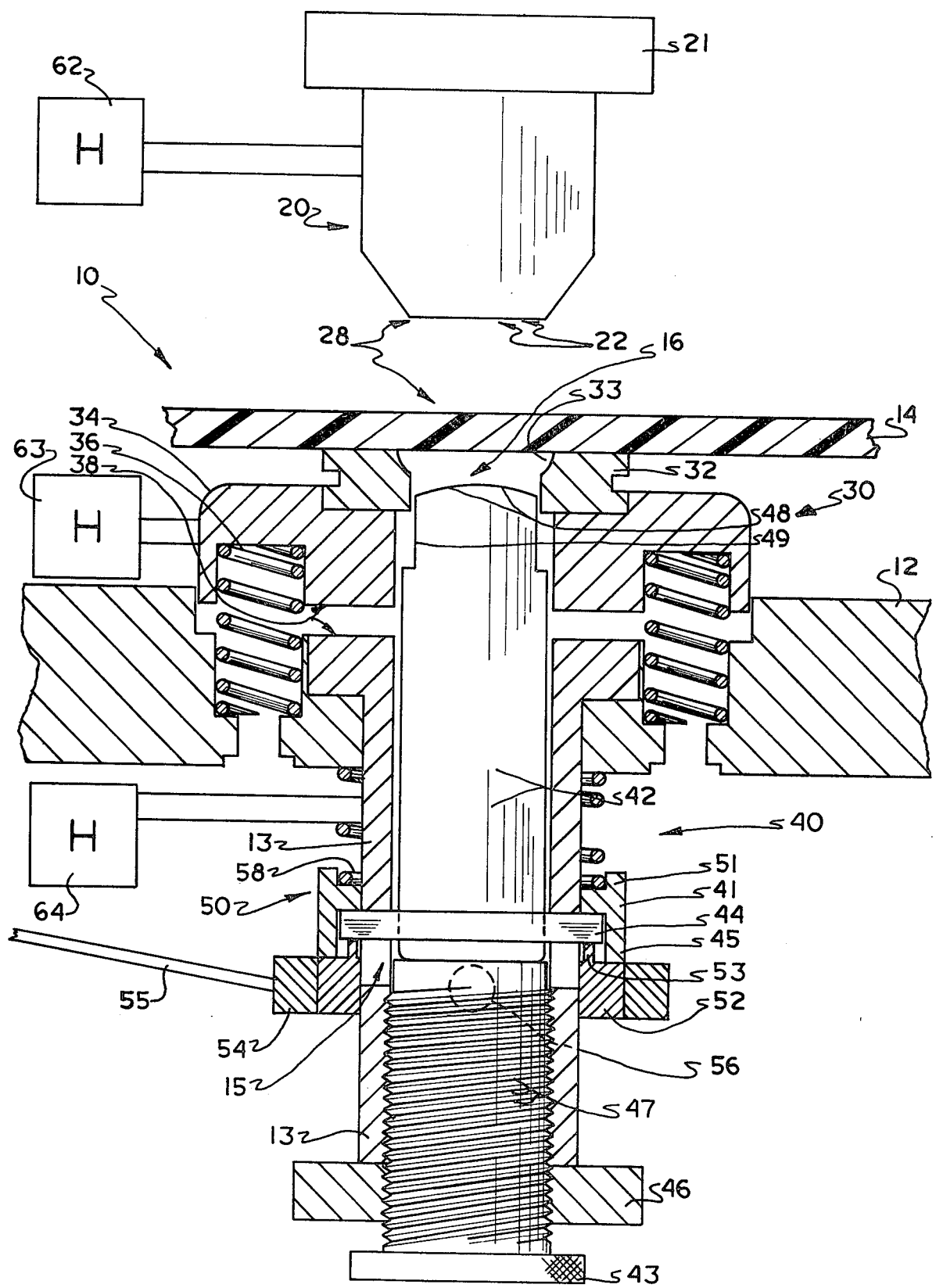
FIG. 1 is an elevational cross-sectional view of the variable volume sample apparatus in position prior to the manipulating and cutting operation; and, FIG. 2 is an elevational cross-sectional view of the variable volume sample apparatus in position just after the cutting operation has occurred.

In order to achieve the objects of the invention, an apparatus for the cutting of elastomeric material has been designed and reference is made to the Figures for an understanding of its components. The variable volume sample apparatus, generally denominated as 10, is composed of a die cutting apparatus, generally denominated as 20, a die receiving apparatus, generally denominated as 30, a volumetric sample adjustment apparatus, generally denominated as 40, and an ejection apparatus 50. These apparatus 20, 30, 40 and 50, during the course of operation, move in relation to anchored upper frame 12 and post housing 13.

The die cutting apparatus 20 is composed of a drive rod 21 having a cutting surface, generally denominated at 22, at its terminus thereon. Cutting surface 22 has an elastomer-manipulative surface which promotes manipulation concentrically outward from the drive rod axis; in this case, an axial protrusion 23, a concentrical recess 24, a peripheral protrusion 25, and a curved contact surface 26. The particular configuration of the cutting surface 22, in combination with volumetric sample adjustment apparatus 40 achieves the volumetric homogeneity of elastomeric material within volumetric cavity 16 before the final cutting operation occurs.

Die receiving apparatus 30 is composed of an interchangeable die 32, having annular groove 33, a die housing 34, tension means 36, which gauge the tension depth 38. The die 32, as supplemented by annular groove 33, die housing 34 and tension means 36 control the force by which the elastomeric material 14 is compressed into the volumetric cavity 16 before cutting to form the elastomeric sample 18. The cavity 16 has a volumetric capacity when die receiving apparatus 30 has contacted frame 12 at full tension depth 38. At that point, the interior dimensions of die 32 and the adjustment position apparatus 40 determine the volume of the cavity 16.

Volumetric sample adjustment apparatus 40 is comprised of skirt ring 41, forming post 42, volumetric adjusting screw 43, pin 44, and locking ring 46. A key feature to the volumetric sample adjustment apparatus 40 is the forming post 42 which may have a narrowed terminus 49 to match the interior dimensions of die 32 and also has a contact surface 48 thereon. The forming post 42 is adjusted in depth by turning the volumetric adjusting screw 43 which has threads 47 which mate with post housing 13. The lower surface of forming post 42 intimately contacts volumetric adjusting screw 43, such that minute adjustments by the turning of the screw 43 achieve a movement in forming post 42 of the same distance.

In order to maintain the position of the volumetric sample adjustment apparatus 40 after the volume of the volumetric cavity 16 has been determined, the locking ring 46 having threads which mate with threads 47 of volumetric adjusting screw 43, is turned to engage the lower surface of the post housing 13. When the locking ring 46 engages the post housing 13, the volumetric adjusting screw 43, and hence the forming post 42 is set in the determined position.

With the interior diameter dimensions of interchangeable die 32 fixed by its shape, the adjustment of forming post 42, which must account for the damped movement of die receiving apparatus 30 to the distance of tension depth 38, determines the capacity of the volumetric cavity 16. The adjustment apparatus 40 is capable of adjusting the volumetric cavity 16 such that the elastomeric samples 18 may differ in mass as small as one gram by the adjustment of apparatus 40. Elastomeric samples 18 are reproducible at specified mass within a tolerance less than one gram. That permits the mass production of elastomeric samples for precision purposes, a real and fundamental object of the invention.

The remaining feature of variable volume sample apparatus 10 is the ejection apparatus 50 which exerts movement upon the forming post 42 but not the volumetric adjusting screw 43. The ejection apparatus 50 is comprised of skirt ring 41, pin 44, spanner ring 52, yoke 54, ejection rod 55, pivot pin 56, and ejection tension means 58. After the elastomeric material 14 is cut into the elastomeric sample 18, it must be removed from the volumetric cavity 16. The sample 18 compressed against contact surface 48 of forming post 42 is removed from die 32 by an upward movement of forming post 42 as precipitated by the ejection apparatus 50. Pin 44, residing in post housing slot 15 passes the lower portion of the forming post 42. Upward movement against the pin 44 by the spanner ring 52 having upper flange 53 forces the upward movement of the forming post 42. This spanner ring 52 is activated by the yoke 54 surrounding it and secured at pivot pin 56. Remote control of the ejection apparatus 50 is accomplished by the ejection rod 55. Protection of the engagement of pin 44 through slot 15 and forming post 42, as well as the engagement of upper flange 53 against pin 44 is accomplished by skirt ring 41 having a lower skirt ring flange 45. The tension necessary to return ejection apparatus to its rest position is accomplished by ejection tension means 58 against skirt ring 41, the means 58 being restrained by upper skirt ring flange 51.

Figure 2:
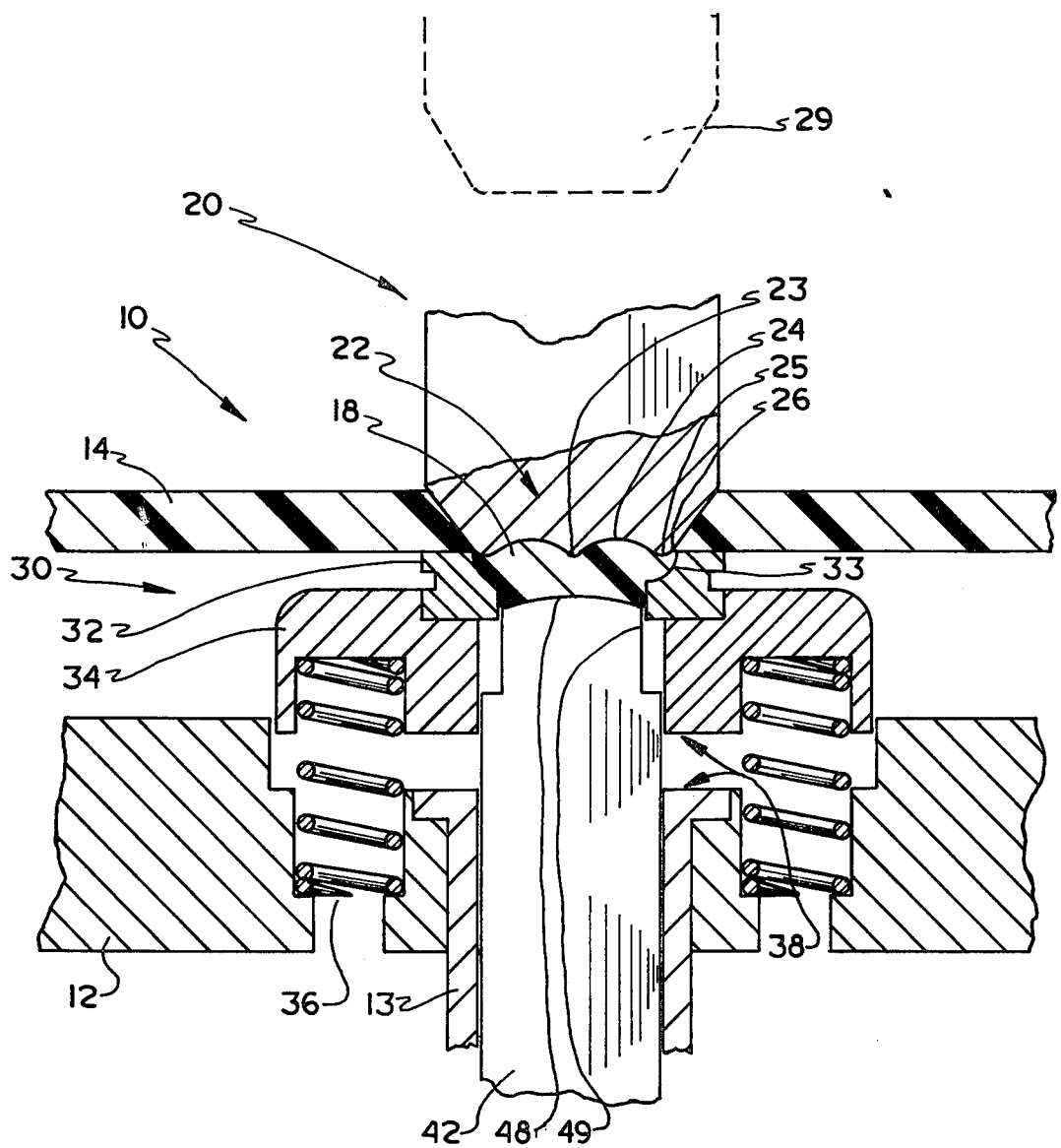

Apparatus 10 may cut the elastomeric material 14 according to the following method. As seen in FIG. 2, after the elastomeric material 14 has been laid across the working surface of apparatus 10, including die receiving apparatus 30 having die 32, the die cutting apparatus 20 may engage the elastomeric material 14. The elevated image of the die cutting apparatus 29 above the elastomeric material 14 indicates a die stroke of approximately 3 inches, denominated as 28.

As the cutting surface 22 engages the elastomeric material 14, the axial protrusion 23 initiates a manipulation of the elastomeric material 14 from the axial point outwardly in a concentric circular arrangement. Within the concentrical recess 24, this manipulation continues according to the natural contours of the recess 24 which is terminated by the peripheral protrusion 25. This manipulation procedure occurs as the cutting surface 22 forces the elastomeric material from the upper surface of die 32, through annular groove 33, into volumetric cavity 16, the cavity of which having been adjusted by volumetric sample adjustment apparatus 40.

The removal of air bubbles and other defects in the resilient elastomeric material 14, as well as air bubbles within cavity 16 itself, is accomplished by the cooperation of the various portions of the cutting surface 22 with the forming post contact surface 48. The forming post contact surface 48, which may have an angled surface from the axis of post 42, matches the force and effect of the movement of the elastomeric material 14 as manipulated by the axial protrusion 23 and concentrical recess 24 of the cutting surface 22. By the time the elastomeric material 14 is severed on the upward stroke at curved contact surface 26, in order to form a volumetric elastomeric sample 18, the entire sample 18 has been worked and manipulated to remove air bubbles and non-homogeneous structure from the axial center outwardly to the periphery prior to the cutting operation.

Downward movement of die receiving apparatus 30, relative to apparatus 40 and post 42, is provided to permit manipulation of material 14 prior to cutting. This movement is damped by tension means 36 to the depth 38 that die housing 34 may move to engage frame 12. At that point, volumetric cavity 16 is finally determined and manipulation of material 14 is completed.

The elastomeric material 14 is manipulated into cavity 16 during the downward stroke 28 of die cutting apparatus 10. Excess material 14 is extruded from cavity 16 through annular groove 33 of die 32. Indeed, groove 33 is shaped to prevent a cutting of material 14 during the downward stroke 28, in order that the pressure of die cutting apparatus 20 is transmitted through material in groove 33 to tension means 36 on die receiving apparatus 30. Further, stroke 28 is of such distance to prevent cutting surface 22 to engage the upper edge of groove 33 of die 32, even to the lowest point in the cycle, defined by depth 38 and stroke 28. No cutting of material 14 occurs during downward movement or at the lowest point of contact between apparatus 30 and frame 12. No cutting of material 14 occurs because material 14 continually extrudes from cavity 16 during downward pressure by cutting surface 22, which is delocalized by the shape of groove 33 and which is also damped by tension means 36. The extruded material 14 remains attached to material 14 within the cavity 16 because the stroke 28, too short to complete a pressurized cutting, ends before engaging groove 33 on apparatus 30 bottomed out to a full, tensioned depth 38. At this point, a thin layer elastomeric material 14 remains between surface 26 and groove 33. After the pressure forcing die cutting apparatus 20 downward has been released, and apparatus 20 retreats, the upward movement of tension means 36 forces the upper edge of annular groove 33 of die 32 against curved contact surface 26, severing the remaining elastomeric material in groove 33 and creating an elastomeric plug 18. The upward cutting operation preserves the uniformity of the die cutting surface 22 and die 32 from aberrations resulting from pressured cutting by the die cutting apparatus 20. The manipulation of the elastomeric material 14 is thereby uniformly maintained in each cycle.

While the manipulation of the elastomeric material 14 by the die cutting surface 22 provides a homogeneous segment of material 14 within the volumetric cavity 16, it is the volumetric sample adjustment apparatus which determines the volume of the material 14 cut into elastomeric sample 18. The adjustment of apparatus 40 is accomplished by the release of locking ring 46 on threads 47 of volumetric adjusting screw 43. After the proper capacity has been determined, the locking ring 46 is tightened against the lower edge of post housing 13. This set position of screw 43 is translated to the forming post contact surface 48 by the substantial contact between forming post 42 and screw 43. Again, minute adjustments in the capacity of the volumetric cavity 16 is accomplished by the above-described adjusting operation. This adjustment apparatus 40 is capable of altering the mass of the elastomeric sample 18 cut within a tolerance of one gram.

After the elastomeric sample has been formed, and the die cutting apparatus 20 has returned the length of its stroke 28 to a position above the die receiving apparatus 30, the elastomeric sample 18 must be removed from the volumetric cavity 16. Ejection apparatus 50 is employed for that purpose. Pin 44, passing through slot 15 of post housing 13 and the lower portion of forming post 42, activates the movement of forming post 42 to force the sample 18 from the cavity 16. Pin 44 is activated by engagement of the upper flange 53 of the spanner ring 52, that ring 52 being further activated by yoke 54 and ejection rod 55 at the pivot pin 56. The contact of upper flange 53 with pivot pin 44 is protected by lower skirt ring flange 45 on skirt ring 41. After ejection apparatus 50 has forced forming post 42 to eject the sample 18 from cavity 16, tension means 58 as constrained by upper skirt ring flange 51 return the ejection apparatus 50 and the forming post 42 to a position where the lower surface of forming post 42 may reengage the upper surface of volumetric adjusting screw 43. Once ejection apparatus 50 has completed its operation, and volumetric sample adjustment apparatus 40 is returned to its set position, the elastomeric material 14 may be shifted on the die receiving apparatus 30 to begin another volumetric cutting operation.

The variable volume sample apparatus 10 is made from sturdy metal alloys well known to those in the die cutting art. Particularly, steel alloys provide strength to withstand the cutting cycle, without altering shape which would affect the volumetric cavity 16 dimensions or the quality of the sample 18 so produced.

The variable volume sample apparatus 10 can be modified to treat the elastomeric material 14 as well as cutting it. Uncured elastomeric material 14 may be cured within volumetric cavity 16 during downward stroke 28 to the lowest point of the cycle by the addition of heating element 62 to drive rod 21 of die cutting apparatus, heating element 63 to die receiving apparatus 30, and heating element 64 to forming post housing 13. The particular elastomeric material 14 to be cured is manipulated and cured as the pressure of die cutting apparatus 20 is maintained. The release of pressure removes apparatus 20 and tension means 36 spring annular groove 33 of die 32 against cutting surface 22, cutting the cured volumetric elastomeric plug 18. Heating elements 62, 63, 64 may be any heat sources known to those skilled in the art which will heat apparatus 10 to temperatures sufficient to cure elastomeric material 14 within cavity 16.

While in accordance with the Patent Statutes, a best mode and preferred embodiment of the invention has been disclosed. the invention is not to be limited thereto or thereby. Consequently, for an appreciation of the scope of the invention, reference is had to the following claims.

What is claimed is:

1. An apparatus for the variable cutting of volumetric samples from elastomeric material, comprising:
    (a) a fixed frame having a forming post housing;
    (b) a die cutting apparatus having a pressured downward stroke, an unpressured upward stroke, a periphery and a surface means for concentrically manipulating the elastomeric material towards said periphery;
    (c) a die receiving apparatus having tension-damping means for tensionally mounting said receiving apparatus on said frame and for damping said downward stroke against the elastomeric material, and having a die with an internal hollow having a dimension; said die having an annular groove at the uppermost area of said internal hollow; and,
    (d) a volumetric sample adjustment apparatus having a movable forming post and adjustment means for moving said forming post, said forming post having a contact surface which resides in said internal hollow of said die, so that said movable forming post and said die dimension determine a volumetric cavity into which the elastomeric material may be manipulated, by said surface means during said downward stroke of said die cutting apparatus, thereby extruding excess elastomeric material between said periphery and said annular groove prior to cutting the material into the volumetric sample by said groove and said periphery during said upward stroke.

2. An apparatus for the variable cutting of volumetric samples of elastomeric material, according to claim 1, wherein said surface means comprises an axial protrusion, and a concentrical recess, and wherein said periphery comprises a peripheral protrusion, and a curved contact surface, said concentrical recess, concentrically contiguous to said axial protrusion, said peripheral protrusion, concentrically contiguous to said concentrical recess and said curved contact surface concentrically contiguous to said peripheral protrusion, so that the elastomeric material is concentrically manipulated from said axial protrusion to said curved contact surface to remove trapped air bubbles and nonhomogeneous forms by extrusion from the material within said volumetric cavity prior to cutting the material into a volumetric sample.

3. An apparatus for the variable cutting of volumetric samples of elastomeric material, according to claim 1, wherein said adjustment means comprises a volumetric adjusting screw and a threaded locking ring, said volumetric adjusting screw having threads which variably engage both said forming post housing and said threaded locking ring and having an upper surface to communicate with said forming post, so that adjusting said screw alters said volumetric capacity;

said threaded locking ring communicating with the bottom surface of said forming post housing, so that said adjusting screw is restrained to the adjusted position.

4. An apparatus for the variable cutting of volumetric samples of elastomeric material, according to claim 1, wherein an ejection apparatus engages said forming post housing having a slot and engages said forming post for the removal of the volumetric sample, said ejection apparatus comprising a pin; a skirt ring; ejection means for moving said pin, said skirt ring, and said forming post; and ejection tension means for returning said ejection apparatus and said forming post to the adjusted position; and said skirt ring having an upper flange to restrain said ejection tension means and a lower flange to restrain said pin, engaged with said forming post, within said slot of said forming post housing.

5. An apparatus for the variable cutting of volumetric samples of elastomeric material, according to claim 4, wherein said ejection means comprises a spanner ring, an ejection rod, a yoke, and a pivot pin, said pivot pin securing said spanner ring and said yoke, said spanner ring having an upper flange communicating with said forming post pin, and said yoke connected with said ejection rod.

6. An apparatus for the variable cutting of volumetric samples of elastomeric material, according to claim 1, wherein said die cutting apparatus, said forming post housing, and said die receiving apparatus have heat sources, so that uncured elastomeric material may be cured prior to cutting the material into volumetric samples.

7. A method for cutting a volumetric sample for elastomeric material, comprising:
(a) placing a section of elastomeric material on a die receiving apparatus, said die receiving apparatus having tension-damping means for damping pressure against the elastomeric material and having a die with an internal hollow having a dimension; said die having an annular groove at the uppermost area of said internal hollow;
(b) adjusting a volumetric sample adjustment apparatus having a movable forming post within a fixed forming post housing and adjustment means for moving said forming post, said forming post having a contact surface which resides in said internal hollow of said die, so that said movable forming post and said die dimension determine a volumetric cavity;
(c) moving a die cutting apparatus into contact with the elastomeric material, said apparatus having a pressured downward stroke, an unpressured upward stroke, a periphery, and surface means for concentrically manipulating the elastomeric material toward said periphery, said surface means having an axis;
(d) manipulating and compressing during said pressured downward stroke a section of the elastomeric material into said volumetric cavity;
(e) extruding the elastomeric material from said volumetric cavity between said groove and said periphery during said pressured downward stroke; and,
(f) cutting the elastomeric material into a volumetric sample of homogeneous form by contacting the upper edge of said groove with said periphery during said unpressured upward stroke.

8. A method for cutting a volumetric sample from elastomeric material, according to claim 7, wherein manipulating and compressing proceeds concentrically from said axis of said surface means.

9. A method for cutting a volumetric sample from elastomeric material, according to claim 7, wherein said manipulating and said compressing into said cavity is damped by said tension-damping means for restraining contact of said die cutting apparatus with said die receiving apparatus at the lowest point of said pressured downward stroke so that said manipulating step is accomplished prior to said cutting step.

10. A method for cutting a volumetric sample from elastomeric material, according to claim 9, wherein said cutting step occurs after said tension damping means have reached greatest compression and begun to expand.

11. A method for cutting a volumetric sample from elastomeric material, according to claim 7, wherein said adjusting comprises loosening a locking ring, turning a threaded adjusting screw to the desired setting, and locking said locking ring.

12. A method for cutting a volumetric sample from elastomeric material, according to claim 7, further comprising the step of ejecting the volumetric sample from the volumetric cavity, said ejecting performed by a pin, a skirt ring, ejection means for moving said pin, said skirt ring, and said forming post, and ejection tension means for returning said forming post to its adjusted position, and said skirt ring having an upper flange to restrain said ejection tension means and a lower flange to restrain said pin, engaged with said forming post, within said slot of said forming post housing.

13. A method for cutting a volumetric sample from elastomeric material, according to claim 7, further comprising the step of heating the uncured elastomeric material, during said manipulating and said compressing and prior to said cutting, with said die cutting apparatus, said forming post housing, and said die receiving apparatus heated by intimate contact with heat sources.

* * * * *